(12) United States Patent
Mano et al.

(10) Patent No.: US 7,537,566 B2
(45) Date of Patent: May 26, 2009

(54) BONE STRENGTH MEASURING INSTRUMENT AND METHOD

(75) Inventors: Isao Mano, Kyoto (JP); Takuji Suzaki, Kyoto (JP); Takahiko Otani, Kyoto (JP)

(73) Assignees: Japan Science and Technology Agency, Saitama (JP); Oyo Electric Co., Ltd., Kyoto (JP); Horiba, Ltd., Kyoto (JP)

( * ) Notice: Subject to any disclaimer, the term of this patent is extended or adjusted under 35 U.S.C. 154(b) by 804 days.

(21) Appl. No.: 11/040,582

(22) Filed: Jan. 21, 2005

(65) Prior Publication Data

US 2005/0182325 A1 Aug. 18, 2005

(30) Foreign Application Priority Data

Jan. 21, 2004 (JP) ............................. 2004-013584
Jul. 2, 2004 (JP) ............................. 2004-196553

(51) Int. Cl.
*A61B 8/02* (2006.01)
(52) U.S. Cl. ..................... 600/442; 600/449; 600/437
(58) Field of Classification Search ............. 600/437, 600/449, 438, 442; 128/661.03
See application file for complete search history.

(56) References Cited

U.S. PATENT DOCUMENTS

| | | | |
|---|---|---|---|
| 4,926,870 A | 5/1990 | Brandenburger | |
| 5,535,750 A * | 7/1996 | Matsui et al. | 600/592 |
| 5,720,290 A * | 2/1998 | Buhler et al. | 600/449 |
| 5,730,135 A | 3/1998 | Otani et al. | |
| 5,806,520 A | 9/1998 | Berger et al. | |
| 5,817,018 A * | 10/1998 | Ohtomo | 600/437 |
| 6,364,837 B1 * | 4/2002 | Mazess et al. | 600/449 |
| 6,371,916 B1 | 4/2002 | Buhler et al. | |

FOREIGN PATENT DOCUMENTS

| | | |
|---|---|---|
| JP | 05-192333 | 8/1993 |
| JP | 06-269447 | 9/1994 |
| JP | 07-100136 | 4/1995 |
| JP | 08-280677 | 10/1996 |

\* cited by examiner

*Primary Examiner*—Eric F Winakur
*Assistant Examiner*—Lawrence N Laryea

(57) ABSTRACT

A bone strength measuring instrument and method is provided for obtaining thickness values of cortical bone, cancellous bone and tissue in a human body part by applying an ultrasonic wave to a measured portion of the human body. Ultrasonic transmitters and receivers can be positioned in contact with the human body to provide a set thickness for the human body while processing the received signals transmitted through and reflected from the human body portions to determine a first wave higher in speed and a second wave lower in speed. Prior to making the measurements, a preliminary measurement procedure can be utilized to optimize the desired measurement site. An acoustic speed of the second wave in a cancellous bone can be assumed to be constant and transit times can be calculated and respective thickness values of the soft tissue of cortical bone and cancellous bone can be determined to indicate the bone strength.

9 Claims, 14 Drawing Sheets

| × | × | × | ○ | ○ | ○ | × | × | × | — |
|---|---|---|---|---|---|---|---|---|---|
| × | × | × | ○ | × | × | × | ○ | × | × |
| × | × | ○ | × | × | ○ | ○ | ○ | ○ | × |
| × | × | × | × | × | ○ | ○ | × | × | × |
| × | × | × | × | × | ○ | ○ | × | × | × |
| × | × | × | ○ | × | × | ○ | ○ | ○ | × |
| × | × | × | × | ○ | ○ | — | — | — | — |
| × | × | × | ○ | — | — | — | — | — | — |
| × | × | ○ | ○ | — | — | — | — | — | — |
| × | × | × | ○ | × | — | — | — | — | — |

○ : two wave-separable

× : two wave-nonseparable

— : out of measurement

Fig. 13

BONE STRENGTH MEASURING INSTRUMENT AND METHOD

BACKGROUND OF THE INVENTION

1. Field of the Invention

This invention relates to a bone strength measuring instrument and method for diagnosing the bone strength in part of a human body by using an ultrasonic wave, and more particularly to provide improvements in precision, reliability and accuracy.

2. Description of Related Art

Recent development and a need for practical use in recent years in the medical profession has encouraged the application of bone strength measuring instruments for measuring bone strength in part of a human body such as a wrist and a heel using an ultrasonic wave. For example, a technique has been known that, as shown in JP Patent No. 2863886, transmission or reception of an ultrasonic wave is conducted through a part of a human body in a state where a pair of ultrasonic probes each including an ultrasonic transmit/receive transducer holds a part of a human body therebetween and signals obtained in this situation are processed to thereby obtain information on the bone such as bone strength and bone density.

In a case where a bone strength of a person is measured, the measurement has generally been conducted on measurement sites such as a wrist or heel thereof, whereas it has been known that much of a cancellous bone exists in a specific site of a human body such as the wrist or heel and which is dissimilar to other sites on the human body thereof. FIG. 15 shows a cross-sectional structure of a wrist 1 as a model in which a cancellous bone 2 is at the center and a cortical bone 3 and a soft tissue 4 are disposed almost concentrically.

A bone strength measuring instrument described in JP Patent No. 2863886 has a construction obtained based on finding that if a measurement site where a cancellous bone exists is irradiated with an ultrasonic wave pulse in a direction of the diametral thereof, the ultrasonic wave is separated into two components different in acoustic speed from each other. To be detailed, an acoustic speed of an ultrasonic wave transmitted through the cancellous bone differs according to a different bone layer arrangement of the cancellous bone, that is between transmission through a porous structure portion and a bone marrow structure portion. As a result, an ultrasonic wave emitted from one ultrasonic probe is separated into two acoustic waves different in speed from each other, that is a first wave higher in acoustic speed and a second wave lower in acoustic speed, which are received by the other ultrasonic probe at different times. For example, an ultrasonic wave is separated into a first wave (a fast wave) and a second wave (a slow wave) in the cancellous bone and the acoustic speed of the first wave depends on specific properties and conditions of the bone. In JP Patent No. 2863886, there is available an advantage that both bone strength and bone quantity can be simultaneously obtained, which previously had been obtained independently of each other in conventional methods.

In a conventional bone strength measuring instrument, a prescribed procedure has been conducted based on preconditions described below in order to obtain thickness values, and properties and conditions of all tissues in wrist 1 as shown in FIG. 15, that is a cancellous bone 2, a cortical bone 3 and a soft tissue 4, respectively.

FIG. 16 schematically shows a construction of a measuring system in a conventional bone strength measuring instrument measuring bone strength present in the interior of a wrist 1 having the above structure, wherein numerical symbols 5 and 6 indicate ultrasonic probes set so as to be in close contact with both sides in the diametral direction of the wrist 1, the body of which, though not shown in a detailed manner, includes: a ultrasonic transmit/receive transducer and an acoustic impedance matching liquid (usually, water is used as the liquid and hereinafter referred to simply as matching water). The ultrasonic probes 5 and 6 are constructed so as to be freely movable linearly in a direction of moving closer to each other or away from each other, that is in a direction, left to right. The ultrasonic probes 5 and 6 are connected to an operation display (not shown) through cables. Note that provided as an operation display is a display unit capable of color display of a measured result and the like and a printer capable of color outputting of a measured result and like.

In FIG. 16, alphabetical symbols a, b, c, d, e and f indicate points on boundaries between the soft tissue 4, the cortical bone 3 and the cancellous bone 2 with which the shortest straight line 7 connecting the ultrasonic probes 5 and 6 intersects sequentially in that order. A symbol Laf indicates a distance between the ultrasonic probes 5 and 6 (hereinafter referred to simply as an inter-probe distance) and Lab and Lef are thickness values of the soft tissue 4, Lbc and Lde are thickness values of the cortical bone 3 and Lcd is a thickness value of the cancellous bone 2.

In a conventional practice, if a speed of an ultrasonic wave emitted from the ultrasonic probe 5 (or 6) is almost constant in the soft tissue 4 and if speeds in the soft tissue portions Lab and Lef is indicated with Vab and Vef than by definition, Vab=Vef=a determined value.

If a speed of the ultrasonic wave is almost constant in the cortical bone 3 and speeds in the cortical bone portions Lbc and Lde is indicated with Vbc and Vde than by definition, Vbc=Vde=a determined value.

The ultrasonic wave is, as described above, separated in the cancellous bone 2 into the first wave (fast) and the second wave (slow), wherein a speed of the first wave depends on the properties and condition (structure) of a bone, while a speed of the second wave is almost constant. Therefore, if a speed of the second wave is indicated with Vs by definition, Vs=a determined value.

In a case where the ultrasonic wave probes 5 and 6 are disposed as shown in FIG. 16, a distance Laf therebetween is measured in advance and Laf=a known determined value.

Now, if in a state shown in FIG. 16, an ultrasonic wave pulse is emitted from both ultrasonic wave probes 5 and 6, a signal shown in FIG. 17(A) is obtained as a signal from waves reflected at the boundaries b and e between the soft tissue 4 and the cortical bone 3 and waves reflected at the boundaries c and d between the cortical bone 3 and the cancellous bone 2. In FIG. 17(A), Tb and Tc are arrival times of reflected waves received by the ultrasonic wave probe 5 and Te and Td are arrival times of reflected waves received by the ultrasonic wave probe 6. If an ultrasonic wave pulse is emitted from one ultrasonic wave probe, for example, the ultrasonic wave probe 5, a signal as shown in FIG. 17(B) is obtained as a transmitted wave.

In the reflected wave shown in FIG. 17(A), the thickness Lab of the soft tissue 4 is obtained from the arrival time Tb from the boundary b received by the ultrasonic wave probe 5. Since the arrival time Tb is a time required to go and return between the boundaries a and b, the thickness Lab is obtained by multiplying a time required for one way Tb/2 by the acoustic speed Vab. That is, $Lab=(Tb/2) \times Vab$.

In a similar way, the thickness Lef of the soft tissue 4 is obtained from the arrival time Te from the boundary e received by the ultrasonic wave probe 6 and $Lef=(Te/2) \times Vef$.

In the reflected wave, a thickness Lbc of the cortical bone 3 is obtained using a difference (Tc−Tb) between an arrival time Tc from the boundary c and an arrival time Tb from the boundary b by the ultrasonic wave probe 5. That is, since the difference (Tc−Tb) is a time required for an ultrasonic wave to go and return between the boundaries b and c, a thickness Lbc of the cortical bone 3 is obtained by multiplying a time for one way (Tc−Tb)/2 by the acoustic speed Vbc $$Lbc=(Tc-Tb)/2\times Vbc$$

In a similar way, a thickness Lde of the cortical bone 3 is obtained using a difference (Td−Te) between an arrival time Td from the boundary d and an arrival time Te from the boundary e by the ultrasonic wave probe. That is, since the difference (Td−Te) is a time required for an ultrasonic wave to go and return between the boundaries e and d, a thickness L be of the cortical bone 3 is obtained by multiplying a time for one way (Td−Te)/2 by the acoustic speed Vde $$Lde=(Td-Te)/2\times Vde$$

Since all of Laf, Lab, Lef, Lbc and Lde are known as described above, a thickness Lcd of the cancellous bone 2 can be obtained. That is, Lcd=Laf−Lab−Lef−Lbc−Lde.

With the above operation conducted, there can be obtained thickness values of all the tissues including the soft tissue 4, the cortical tissue 3 and the cancellous bone 2.

As understood from the above description, in a conventional bone strength measuring apparatus, thickness values of the cortical bone 3 and the cancellous bone 2 are calculated using arrival times Tc and Td of reflected waves from the boundaries c and d between the cortical bone 3 and the cancellous bone 2. However, the inventors have found through research, it is not necessarily easy to detect the reflected waves and rather difficult to do so in some case. Therefore, according to the above calculation method, there has been a cases where thickness values of the cortical bone 3 and the cancellous bone 2 and the like cannot be obtained with good precision, with the result that in such a case, there cannot be obtained certain information on properties and a condition of a bone quantity, a bone strength or the like.

In a conventional bone strength measuring instrument, there has been a case where thickness values of tissues cannot be necessarily obtained with certainty at a site where a cancellous bone 2 does not exist, for example a wrist or a heel, with the result that no reliable information is obtained on the properties and conditions such as bone quantity and bone strength.

Thus there exists a need in instruments for measuring bone density to provide improvements in precision, reliability and accuracy to meet the demands of an aging population.

SUMMARY OF THE INVENTION

The present invention has been made in light of the above circumstances and it is an object of the invention to provide a bone strength measuring instrument capable of accurately obtaining thickness values of a cortical bone and a cancellous bone even in those cases where difficulty may be encountered in detecting a reflected wave from a boundary between the cortical bone and the cancellous bone to thereby obtain a high precision result of evaluation of a bone strength. It is a second object of the invention to provide a bone strength measuring instrument capable of obtaining reliable thickness Values of tissues at sites where no cancellous bone exists to thereby obtain a high precision result of evaluation of a bone strength.

In a case where a measurement of a bone strength or the like is desired in part of a human body, it is also desirable that a measurement region at the measurement site be determined. The reason therefore is that if a measurement site is different according to a person, a measurement result cannot be meaningfully compared with each other and if a measurement site is different for each time of measurement even on the same person, a change in measured value over a time period cannot be correctly traced, thereby preventing a definitive diagnosis.

Therefore, in a case where bone strength is to be diagnosed in a part of a human body using an ultrasonic wave, a proposal has been made to improve the method for conducting measurement of a bone strength, as shown in JP Patent No. 3019580, where a preliminary measurement is conducted using an ultrasonic wave prior to a main measurement using an ultrasonic wave and a measurement region in the main measurement is set based on a result of the preliminary measurement, followed by the main measurement.

Since in the method disclosed in JP Patent No. 3019580, a signal analysis is conducted only on a transmitted wave passing through part of a human body, the present method is better in precision setting of a measurement region as compared with a conventional bone measurement technique of this kind, but with an remaining requirement for improvement on the following aspect.

That is, measurement of a bone strength or the like has been indispensable in diagnosis of osteoporosis or the like and a density of a cancellous bone included comparatively much in quantity in a wrist or a heel has been measured in order to conduct measurement of a bone density or the like in a comparative simple way, whereas in the method taught in JP Patent No. 3019580, a signal analysis is conducted only with a transmitted wave passing through part of a human body, in which difficulty is encountered in conducting precise measurement of a bone strength in a detailed way in part of a human body including a cancellous bone.

The present invention has been made in light of the above circumstances and it is a third object of the invention to provide a bone strength measuring instrument capable of determining a desired measurement region automatically and precisely in measuring a bone strength and irradiating the determined measurement region with an ultrasonic wave with certainty to thereby become excellent in reliability and reproducibility.

The invention is directed to a bone strength measuring instrument, which transmits/receives an ultrasonic wave to/from part of a human body in a state where the part of the human body is held between a pair ultrasonic probes each containing an ultrasonic transmission/reception transducer and an acoustic impedance matching liquid, and processes signals generated upon transmission/reception of the ultrasonic wave, thereby measuring a bone strength in the part of the human body. The processing of the measured signals being constituted in such a manner that from among a first wave which is obtained from the ultrasonic wave probe and is high in speed upon passing through one of the paths in a cancellous bone and a second wave which is also obtained from the ultrasonic wave probe and is low in speed thereupon, an acoustic speed of the second wave in the cancellous bone is assumed as constant. The diagnosis operation is performed using the acoustical speed and arrival times of the second wave to the ultrasonic wave probe; and respective thickness values of a soft tissue, a cortical bone and the cancellous bone in the part of a human body are obtained.

In order to achieve another object, the present invention is directed to a bone strength measuring instrument, which transmits/receives an ultrasonic wave to/from part of a human body in a state where the part of the human body is held between a pair ultrasonic probes each containing an ultrasonic transmission/reception transducer and an acoustic impedance matching liquid, and processes signals generated upon transmission/reception of the ultrasonic wave, thereby measuring a bone strength in the part of the human body, characterized by being constituted in such that an operation is performed using the acoustic speed of the second wave and the arrival times of reflected waves to obtain an acoustic speed in the cortical bone; and a property and condition of the cortical bone are obtained based on the acoustic speed in the cortical bone and a property and condition of the cancellous bone are obtained based on the second wave in the cancellous bone.

The thickness values of the cortical bone and the cancellous bone can be obtained with simplicity by assuming an acoustic speed of the second wave in the cancellous bone is constant, even if it is difficult to detect reflected waves reflected on the boundary between the cortical bone and the cancellous bone, thereby enabling a high precision result of evaluation of a bone strength to be obtained.

A speed of the ultrasonic wave in the cortical bone need not be determined in advance, measurement can be conducted on arrival times of reflected waves reflected on the boundary between the cortical bone and the cancellous bone and an operation is performed using an acoustic speed of the second wave and arrival times of the reflected waves to thereby obtain an acoustic speed in the cortical bone, thereby enabling a property and condition of the cortical bone to be attained with certainty.

An acoustic speed of the second wave need not be determined in advance, when the first wave higher in speed and the second wave lower in speed is transmitted through a path in the cancellous bone and measurement is conducted on arrival times of the second wave and arrival times of reflected waves reflected on the boundary of the cortical bone and the cancellous bone to obtain the acoustic speed of the second wave in the cancellous bone using the arrival times, thereby enabling details of information on the interior of the cancellous bone, especially an organic material between bones to be attained.

A preliminary measurement can be conducted prior to a main measurement by transmitting and receiving an ultrasonic wave through a part of a human body including the cancellous bone to set a measurement region and based on a result of the preliminary measurement, to conduct the main measurement in the measurement region, to process a signal obtained in the main measurement in a logic and arithmetic operation section and to thereby obtain information such as a bone strength in the part of a human body. Accordingly, not only is a signal obtained in the preliminary measurement processed to thereby obtain an attenuation map indicating a degree of attenuation of a transmitted ultrasonic wave, but it is also determined whether or not the first wave higher in speed and the second wave lower in speed separated from the ultrasonic wave can be discriminated from each other to then set the measurement region for the main measurement based on the determination and the attenuation map.

In a case where the part of a human body including the cancellous bone is a wrist, consideration may be given to a connection point between the radius and ulna obtained based on the attenuation map in setting of the measurement region for the main measurement.

The invention is further directed to a bone strength measuring instrument in which a preliminary measurement is conducted prior to a main measurement transmitting and receiving an ultrasonic wave through part of a human body including a cancellous bone to set a measurement region based on a result of the preliminary measurement, to conduct the main measurement in the measurement region, to process a signal obtained in the main measurement in a logic and arithmetic operation section and to thereby obtain information such as a bone strength in the part of a human body, wherein not only is a signal obtained in the preliminary measurement processed to thereby obtain a speed map indicating a speed distribution of a transmitted ultrasonic wave passing through the part of a human body, but it is also determined whether or not the first wave higher in speed and the second wave lower in speed are separated from the ultrasonic wave and can be discriminated from each other and to then set the measurement region for the main measurement based on the determination and the speed map.

In a case where the part of a human body is a wrist, a distance from the connection point between the radius and ulna obtained based on the speed map in setting of the measurement region for the main measurement is stored and the distance may be used in setting of a measurement region for the next measurement.

In the present invention not only is a signal obtained in the preliminary measurement and processed to thereby obtain the attenuation map indicating a degree of attenuation of a transmitted ultrasonic wave, but it is also determined whether or not a first wave higher in speed and a second wave lower in speed from the transmitted ultrasonic wave can be discriminated from each other to thereby set a measurement region for the main measurement based on the determination and the attenuation map. Accordingly, in the measurement of a bone strength, a desired measurement region can be irradiated with a ultrasonic wave with certainty and the measurement of a bone strength can be conducted precisely in a detailed way. Hence, according to the invention, the main measurement conducted based on the preliminary measurement can be conducted with both simplicity and convenience, thereby enabling a measurement of a bone strength with excellency in reliability and reproducibility.

In the case where the part of a human body including the cancellous bone is a wrist, a distance from the connection point between the radius and ulna obtained based on the attenuation map in the setting of the measurement region for the main measurement is stored and the distance is used in setting of a measurement region for the next measurement. Data of a distance is stored in a data memory of, for example, and displayed by relating the data of distance to individual data such as the name of a patient, the data of a distance stored is, in the next measurement, used without conducting a procedure obtaining a reference point starting from the preliminary measurement to thereby enable a measurement region for a main measurement to be set, leading to an effect of enabling the measurement region to be set with simplicity and convenience.

In the case where a signal obtained in the preliminary measurement is processed to thereby obtain the speed map indicating a distribution of speeds of transmitted ultrasonic waves passing through the part of a human body, it is possible to combine the speed map with the determination and to then set a measurement region of the main measurement.

BRIEF DESCRIPTION OF THE DRAWINGS

FIGS. 3(A) and 3(B) are waveform diagrams of ultrasonic waves in a first example, wherein FIG. 3(A) shows a reflected wave while FIG. 3(B) shows a transmitted wave;

FIGS. 4(A) and 4(B) are waveform diagrams of ultrasonic waves in second and third examples, wherein FIG. 4(A) shows a reflected wave while FIG. 4(B) shows a transmitted wave;

FIG. 13 is a representation showing a two wave-separable area map;

FIGS. 17(A) and 17(B) show simplified waveform diagrams of conventional ultrasonic waves, wherein FIG. 17(A) shows a reflected wave while FIG. 17(B) shows a transmitted wave.

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

Reference will now be made in detail to the preferred embodiments of the invention which set forth the best modes contemplated to carry out the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details. In other instances, well known methods, procedures, components, and circuits have not been described in detail as not to unnecessarily obscure aspects of the present invention.

Figure 1:
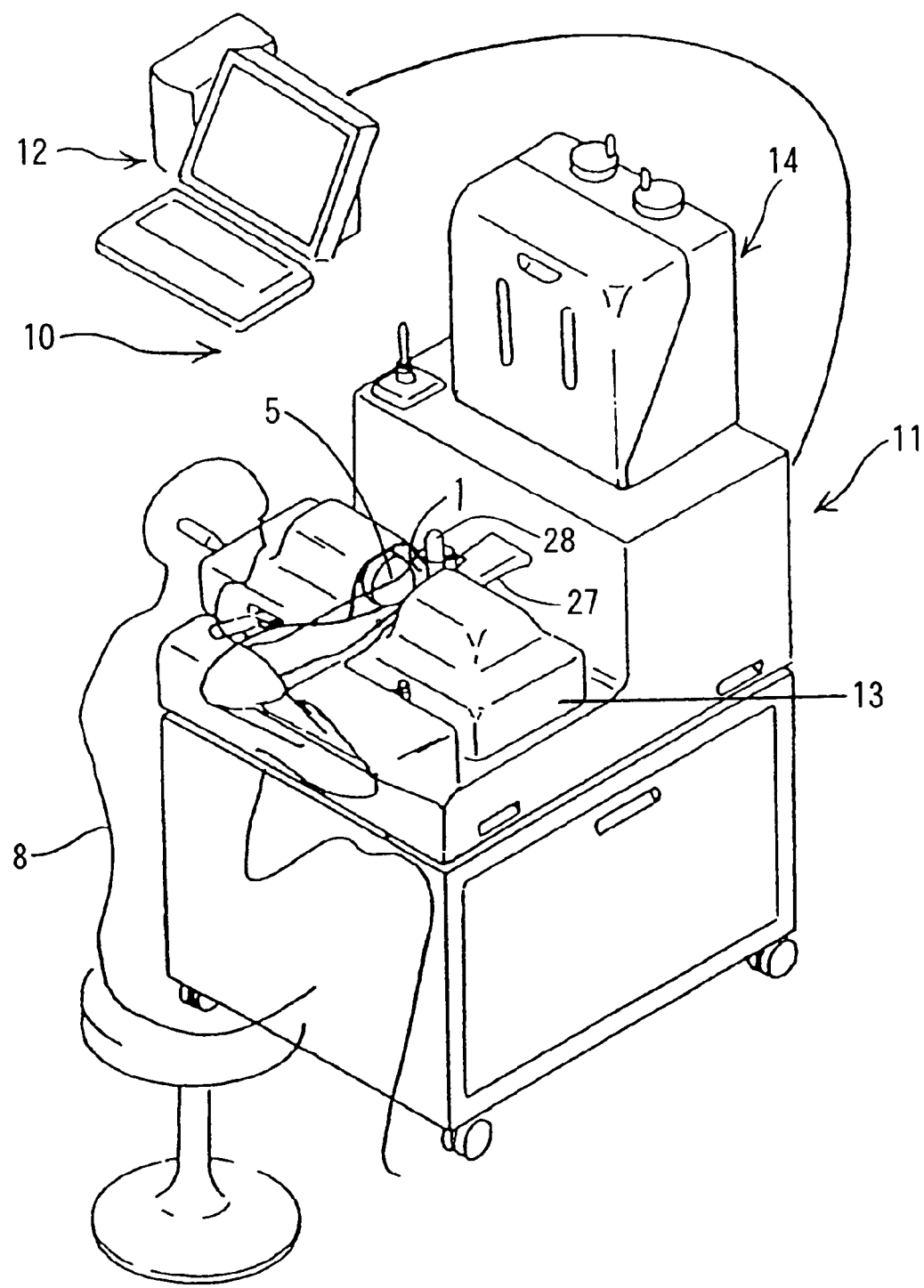
FIG. 1 is a view schematically showing an overall construction of a bone strength measuring instrument of the present invention.

FIGS. 1 to 3(A) and 3(B) show a first example of the present invention. FIG. 1 schematically shows a view of an overall construction of a bone strength measuring instrument 10 and includes a measuring apparatus 11 and an operation display 12 in a broad sense, which is constructed so that evaluation of a bone can be done on a wrist (part of a human body) 1 of a person (a patient) 8, for example.

The measuring apparatus 11, of which a detailed description is omitted, includes: a measuring unit 13 formed in the front side as a measuring section, in which ultrasonic wave probes 5 and 6 are provided that can hold a wrist 1 placed on an arm rest 27 therebetween and can transmit and/or receive a prescribed ultrasonic wave in a state where the wrist 1 is fixedly held stationary therebetween. The measuring apparatus 11 scans a prescribed site of the wrist 1 with the ultrasonic probes 5 and 6 two-dimensionally at a predetermined proper spacing between adjacent measuring points according to a control signal from an operation display 12 to thereby enable a prescribed range of the wrist 1 to be measured two-dimensionally. Note that a numerical symbol 14 indicates an acoustic impedance matching liquid supply section to supply a prescribed acoustic impedance matching liquid to the ultrasonic probes 5 and 6 so as to ensure the ultrasonic probes 5 and 6 are in close contact with both opposite surfaces of the wrist 1. A numerical symbol 28 indicates a grip rod provided to the measuring unit 26 and the grip rod 28 is gripped with fingers of the left hand placed on the arm rest 27, thereby enabling the wrist 1 to be held on the arm rest 27 in a prescribed state.

Figure 16:
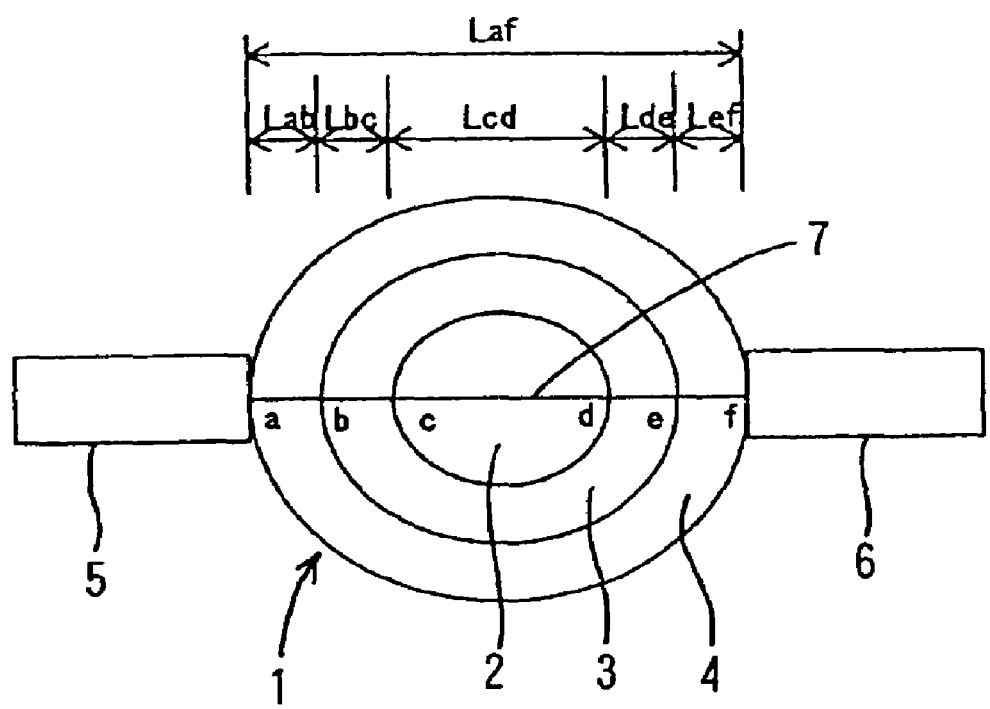
FIG. 16 is a view schematically showing a construction of a measuring system where bone strength measurement is conducted.

FIG. 2 shows schematically a construction of a measuring system in a case where bone measurement is conducted using the bone strength measuring instrument 10 and substantially does not differ from FIG. 16, which is described above, and since in FIG. 2, the same symbols as those attached in FIG. 16 indicate the same constituents, and further descriptions thereof are omitted. In a conventional practice, an ultrasonic wave emitted by the ultrasonic probe 5 (or 6) is almost constant in speed in a soft tissue 4 and if speeds in the soft tissue portions Lab and Lef are indicated with Vab and Vef, then;

$Vab=Vef=$ a determined value.

Speeds of the ultrasonic wave is almost constant in a cortical bone 3 and if speeds in a cortical bone portions Lbc and Lde are indicated with Vbc and Vde, then;

$Vbc=Vde=$ a determined value.

The ultrasonic wave is, as described above, separated into a first wave (a fast wave) and a second wave (a slow wave) in the cancellous bone 2 and the speed of the first wave, which depends on properties and a condition (a structure) of the bone, while the speed of the second wave is almost constant. Therefore, if the speed of the second wave is indicated as Vs, $Vs=$ a determined value.

Figure 2:
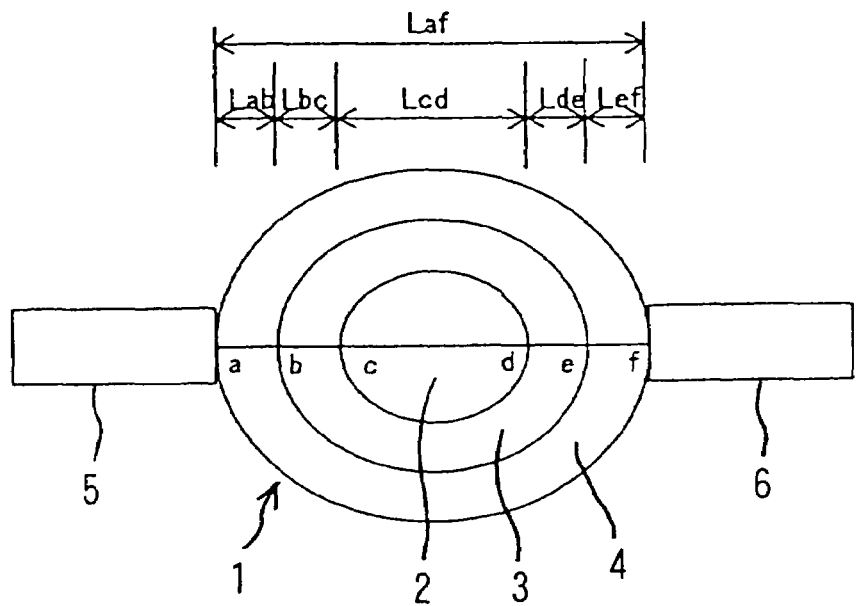
FIG. 2 is a representation schematically showing a construction of a measuring system in a case where bone measurement is conducted using a bone strength measuring instrument.

In a case where the ultrasonic probes 5 and 6 are arranged as shown in FIG. 2, a distance Laf therebetween is measured in advance and $Laf=$ a determined value.

Figure 3A:
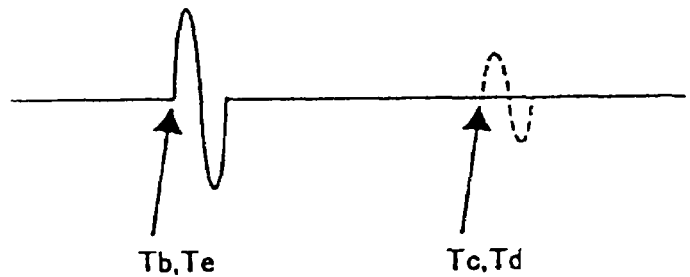
Figure 3B:
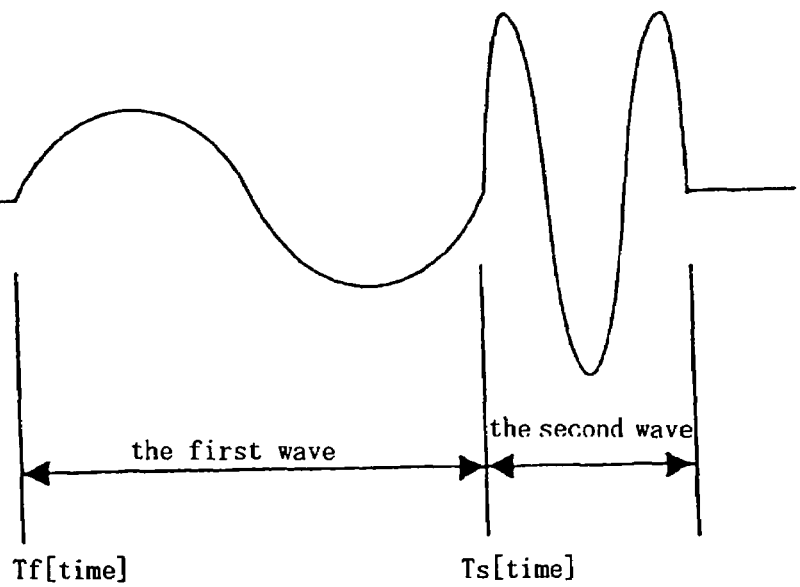

Now, in a case where, for example, in a state shown in FIG. 2, ultrasonic pulses are emitted from both of the ultrasonic probes 5 and 6, a waveform shown in FIG. 3(A) is obtained as a signal from waves reflected on the boundaries b and e between the soft tissue 4 and the cortical bone 3 and the boundaries c and d between the cortical bone 3 and the cancellous bone 2. In FIG. 3(A), Tb and Tc indicate arrival times of reflected waves received by the ultrasonic probe 5 and Te and Td indicate arrival times of reflected waves received by the ultrasonic probe 6. In a case where an ultrasonic pulse is emitted from one ultrasonic probe, for example the ultrasonic probe 5, a signal of a transmitted wave as shown in FIG. 3(B) is obtained.

In the reflected waves shown in FIG. 3(A), a thickness Lab of the soft tissue 4 is obtained using the arrival time Tb from the boundary b received by the ultrasonic probe 5. Since the arrival time Tb is a time to go and return between the boundaries a and b, the thickness $L_{ab}$ is obtained by multiplying a time in one way Tb/2 by the acoustic speed Vab. That is, $$Lab=(Tb/2)\times Vab.$$

A thickness $L_{ef}$ of the soft tissue 4 is similarly obtained from the arrival time Te from the boundary e received by the ultrasonic probe 6 as follows:

$$Lef=(Te/2)\times Vef.$$

On the other hand, a transmitted wave is, as shown in FIG. 3(B), separated into the first wave and the second wave by passing through the cancellous bone 2 and measurement is conducted especially on an arrival time Ts of the second wave. Of the arrival time Ts, a time required for passing through the soft tissue 4 is (Tb/2)+(Te/2) from the results of reflected waves.

A time required to pass through the cortical bone 3 of the second wave is $(L_{bc}+Lde)/Vbc$.

A time required for passing through the cancellous bone 2 of the second wave is (Laf−Lab−Lbc−Lde−Lef)/Vs.[=Lcd/Vs]

The above relations are integrated as follows:

$$Ts=(Tb/2)+(Te/2)+(Lbc+Lde)/Vbc+(Laf-Lab-Lbc-Lde-Lef)/Vs$$

Then $$Ts=(Tb/2)+(Te/2)+(Lbc+Lde)/Vbc+\{Laf-(Lab+Lbc+Lde+Lef)\}/Vs$$

Then, $$Ts=(Tb/2+Te/2)+(Lbc+Lde)\{(1/Vbc)-(1/Vs)\}+\{Laf-(Lab+Lef)\}/Vs.$$

The above integrated relations are further transformed and thereby the following relations are given:

$$(Lbc+Lde)\{(1/Vbc)-(1/Vs)\}=Ts-(Tb/2)+(Te/2)-\{Laf-(Lab+Lef)\}/Vs.$$

Therefore, $$(Lbc+Lde)=[Ts-(Tb/2)+(Te/2)-\{Laf-(Lab+Lef)\}/Vs]/\{(1/Vbc)-(1/Vs)\}.$$

Thus, a thickness of the cortical bone 3 is obtained.

A thickness Lcd of the cancellous bone 2 is expressed by Lcd=Laf−(Lab+Lef+Lbc+Lde) and since terms of the right side of this equation are all obtainable, a thickness $L_{cd}$ of the cancellous bone 2 is also obtained. Calculation of the above equations give thickness values of all the tissues including the soft tissue 4, the cortical bone 3 and the cancellous bone 2.

Note that since an acoustic speed Vab(=Vef) in the soft tissue 4 and an acoustic speed $V_s$ of the second wave are altered slightly by temperature, it is recommended to measure a temperature of a measurement site (in this example, a wrist 1) and to correct the speeds based on the measured temperature. As another method, it is recommended to obtain an acoustic speed Vab(=Vef) in the soft tissue 4 and an acoustic wave Vs of the second wave by measurement on a transmitted wave and a reflected wave in a simple structure (of only a soft tissue, or of only a soft tissue, a cortical bone and a bone marrow).

In the above first example, a speed of the second wave Vs is assumed constant, while in a case where Tc and Td can be measured using reflected waves, thickness values of all the tissues including the soft tissue 4, the cortical bone 3 and the cancellous bone 2 can be obtained without determining acoustic speed Vbc(=Vde) in the cortical bone 3 in advance, or without determining an acoustic speed Vs of the second wave. Description will be given of the procedures as second and third examples below.

Figure 4A:
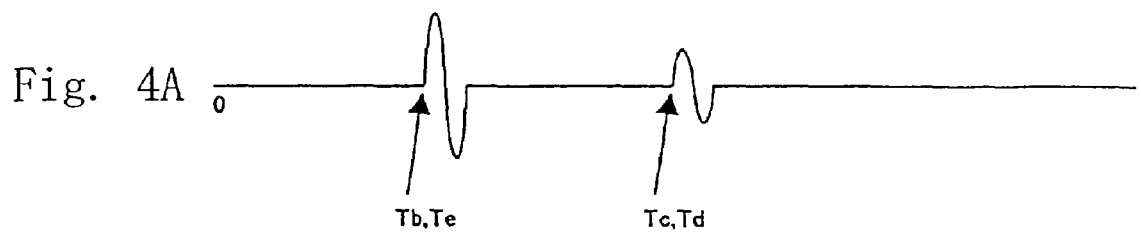
Figure 4B:
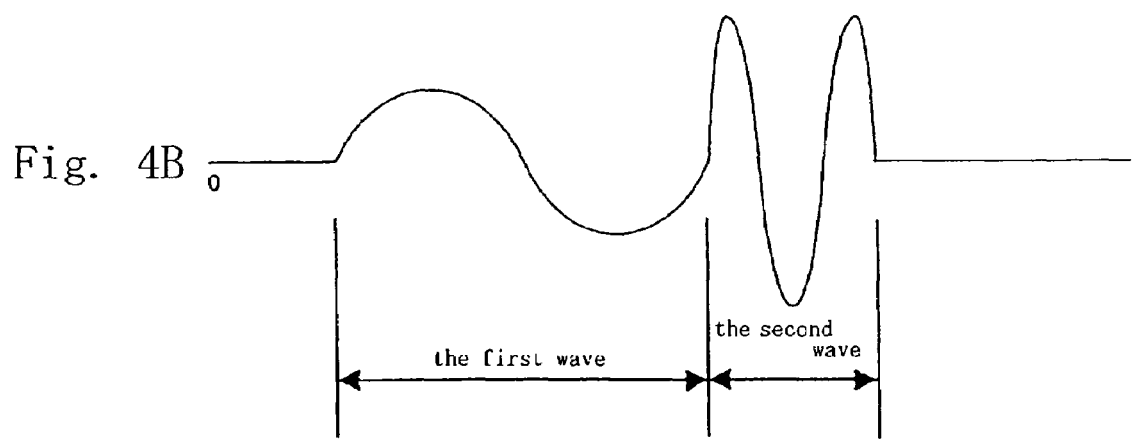

First of all, description is given of the second example, in which case a reflected wave and a transmitted wave are shown in FIGS. 4(A) and 4(B).

The bone portions (Lbc+Lcd+Lde) is given by the following equation using a reflected wave:

$$Lbc+Lcd+Lde=Laf-\{(Tb+Te)/2\}\times Vab \quad (1)$$

Of an arrival time Ts of the second wave, a time required for passing through the cancellous bone 2 is given by Ts−(Tc+Td)/2 from the result of a reflected wave and a thickness Lcd of the cancellous bone 2 is given by $$Lcd=\{Ts-(Tc+Td)/2\}\times Vs] \quad (2)$$

Since a thickness (Lbc+Lde) of the cortical bone 3 is a difference between the above two equations, it is given by—

$$Lbc+Lde=[Laf-\{(Tb+Te)/2\}\times Vab-\{Ts-(Tc+Td)/2\}\times Vs] \quad (3)$$

On the other hand, a time required for passing through the cortical bone 3 is given by (Tc−Tb+Td−Te)/2 from the result of a reflected wave and an acoustic speed Vbc(=Vde) in the cortical bone 3 is given from the result of a reflected wave and the above equation (3) by $$Vbc=[Laf-\{(Tb+Te)/2\}\times Vab-\{Ts-(Tc+Td)/2\}\times Vs]/\{(Tc-Tb+Td-Te)/2\} \quad (4)$$

That is, even if an acoustic speed Vbc(=Vde) in the cortical bone 3 is not determined in advance, an acoustic speed Vbc (=Vde) can be obtained by performing an operation as described above, based on which the properties and a condition of the cortical bone 3 can be obtained.

Note that while in the second example, it is assumed that the cancellous bone 2 exists, the present invention is not limited thereto and an acoustic speed in the cortical bone 3 can also be similarly obtained at a site where no cancellous bone 2 exists (for example, the interior of the cortical bone 3 is made out of only an organic material such as a bone marrow). In a case where no cancellous bone 2 exists, an acoustic impedance is definitely different between the cortical bone 3 and the organic material; therefore, it is easy to detect Tc and Td using a reflected wave. Note that in this case, the first wave does not exist in a transmitted wave and only the second wave is propagated.

Description will be given then of the third example and in this case as well, a reflected wave and a transmitted wave show the waveforms of FIGS. 4(A) and 4(B), respectively.

A time for passing through the soft tissue 4 is (Tb+Te)/2 and a thickness (Lab+Lef) is given by $$Lab+Lef=\{(Tb+Te)/2\}\times Vab \quad (11)$$

A time for passing through the cortical bone 3 is (Tc−Tb+Td−Te)/2 from the result of a reflected wave and a thickness Lbc+Lde of the cortical bone 3 is given by $$Lbc+Lde=\{(Tc-Tb+Td-Te)/2\}\times Vbc \quad (12)$$

A thickness Lcd of the cancellous bone 2 is given by $$Lcd=Laf-(Lab+Lbc+Lde+Lef) \quad (13)$$

Therefore, when relations of the equations (11) and (12) are substituted into the equation (13), the following relation is given:

$$Lcd=Laf-\{(Tb+Te)/2\}\times Vab-\{(Tc-Tb+Td-Te)/2\}\times Vbc \quad (14)$$

Of an arrival time Ts of the second wave, a time for passing through the cancellous bone 2 is given by Ts−(Tc+Td)/2 and an acoustic speed Vs of the second wave is given by $$Vs=Lcd/\{Ts-(Tc+Td)/2\}$$

Then, from the equation (14), $$Vs=[Laf-\{(Tb+Te)/2\}\times Vab-\{(Tc-Tb+Td-Te)/2\}\times Vbc]/\{Ts-(Tc+Td)/2\} \quad (15)$$

That is, an acoustic speed Vs of the second wave can be obtained by performing the operation as described above even if the acoustic speed Vs is not determined in advance and detailed information on the interior of the cancellous bone 2, especially on an organic material between bones can be obtained based on the acoustic speed Vs of the second wave.

While in the third example, it is assumed that the cancellous bone 2 exists, the invention is not limited to the case of the presence of the cancellous bone 2 and an acoustic speed Vs of the second wave can also be similarly obtained at a site where no cancellous bone 2 exists (for example, only an organic material such as bone marrow exists inside the cortical bone 3). In a case where no cancellous bone 2 exists, an acoustic impedance is definitely different between the cortical bone 3 and an organic material; therefore, Tc and Td can be detected with ease using a reflected wave. Note that in the case of a transmitted wave, no first wave exists and only the second wave exists.

While in the above examples, a measurement site is scanned two-dimensionally with the ultrasonic probes 5 and 6, the invention is not limited to such a case and can be similarly applied to a so-called ultrasonic phased array type.

Figure 5:
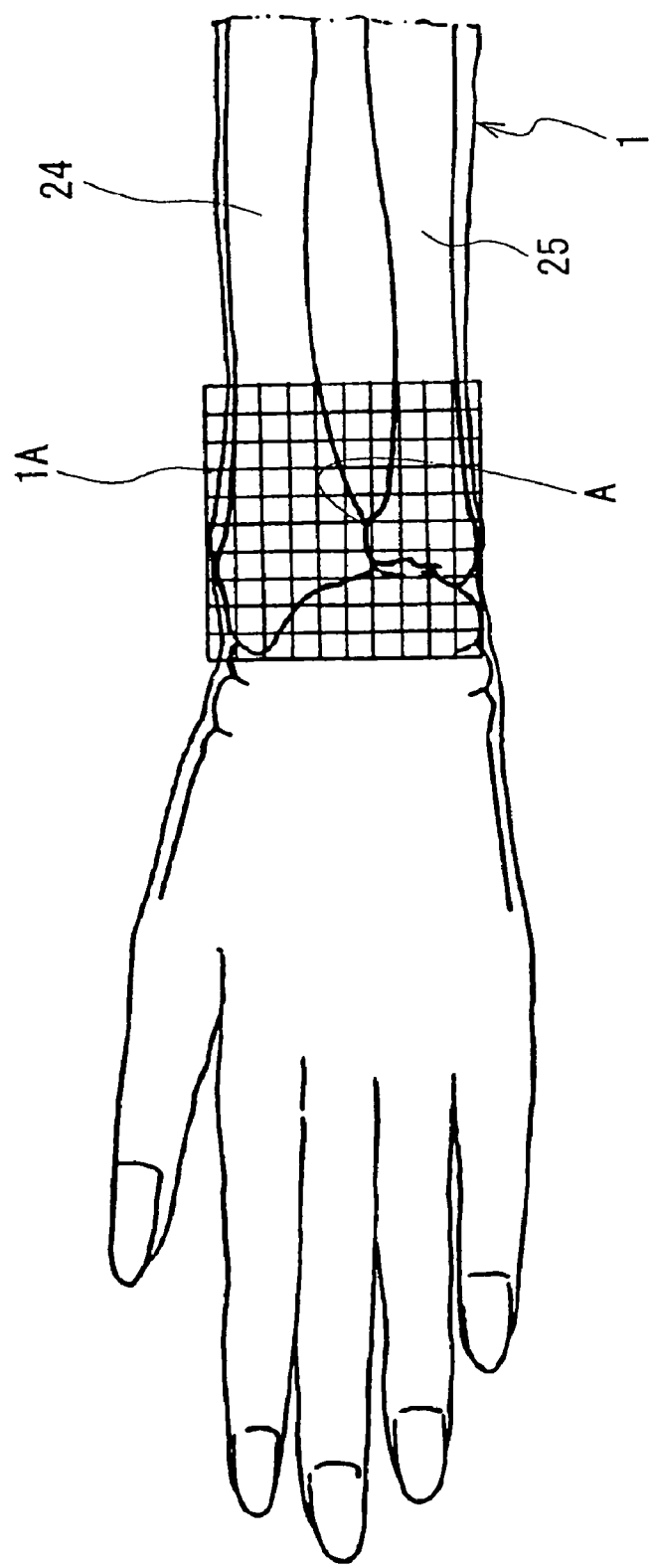
FIG. 5 is a view fluoroscopically showing an example of a measuring site on a subject to be measured by the bone strength measuring instrument.

FIGS. 1 and 5 to 13 show a fourth example of the invention. FIG. 5 shows schematically a fluoroscopic view of a structure of a wrist 1 and the example shown in the diagram is a left wrist and a numerical symbol 24 indicates a radius and 25 an ulna.

Figure 6:
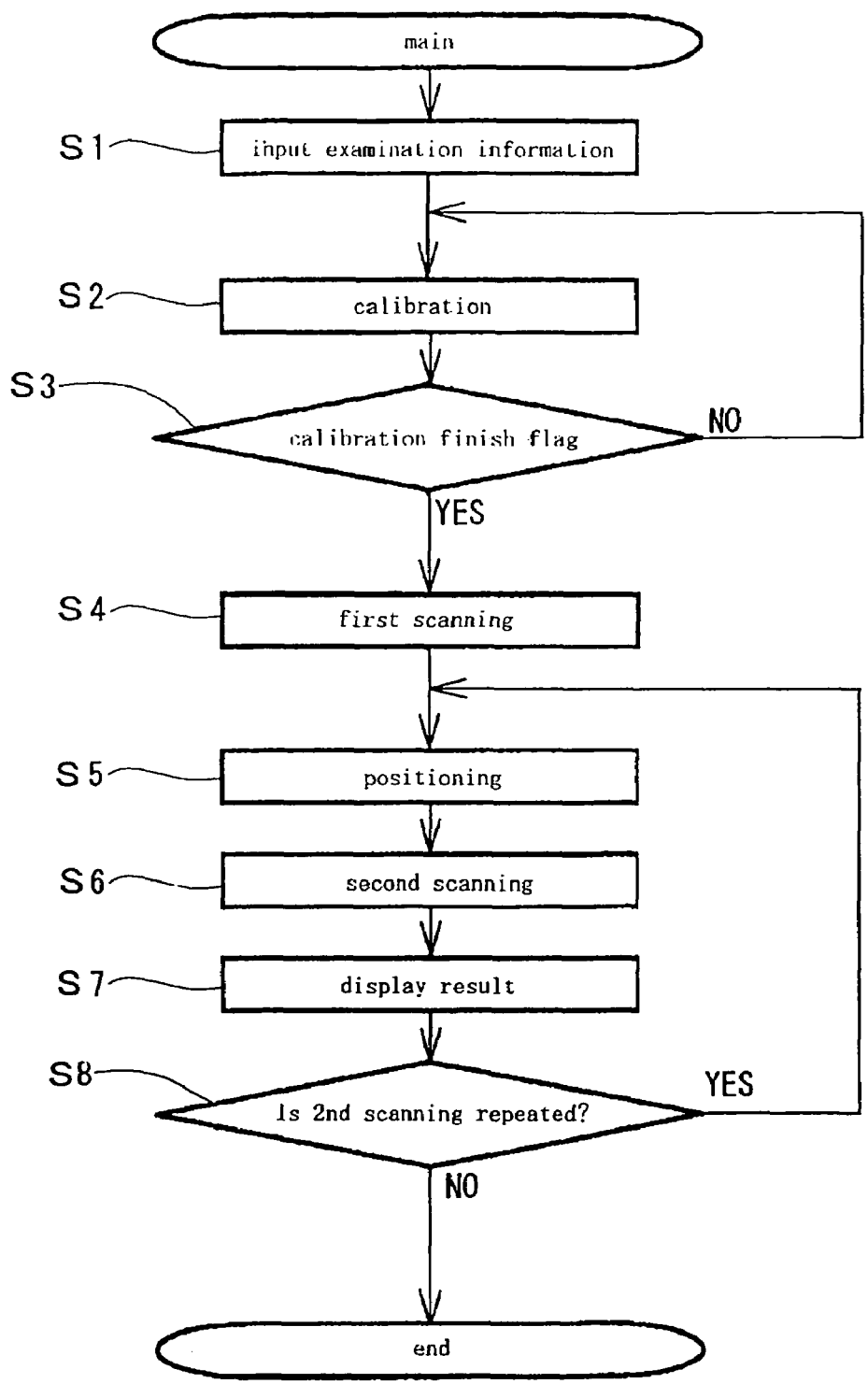
FIG. 6 is a flowchart for describing contents of a measuring procedure with the bone strength measuring instrument.
Figure 7:
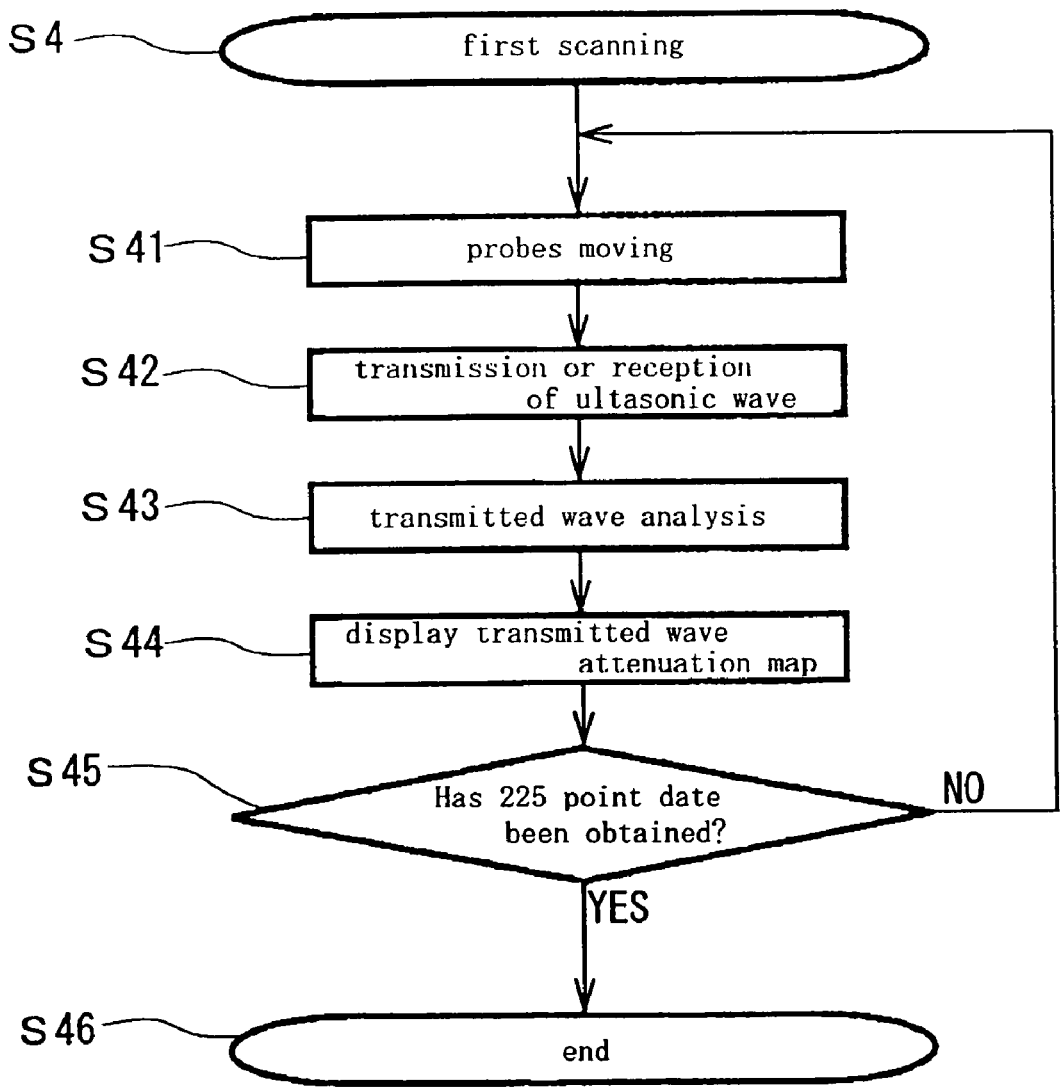
FIG. 7 is a flowchart for describing contents of a first scanning in the measuring procedure.
Figure 8:
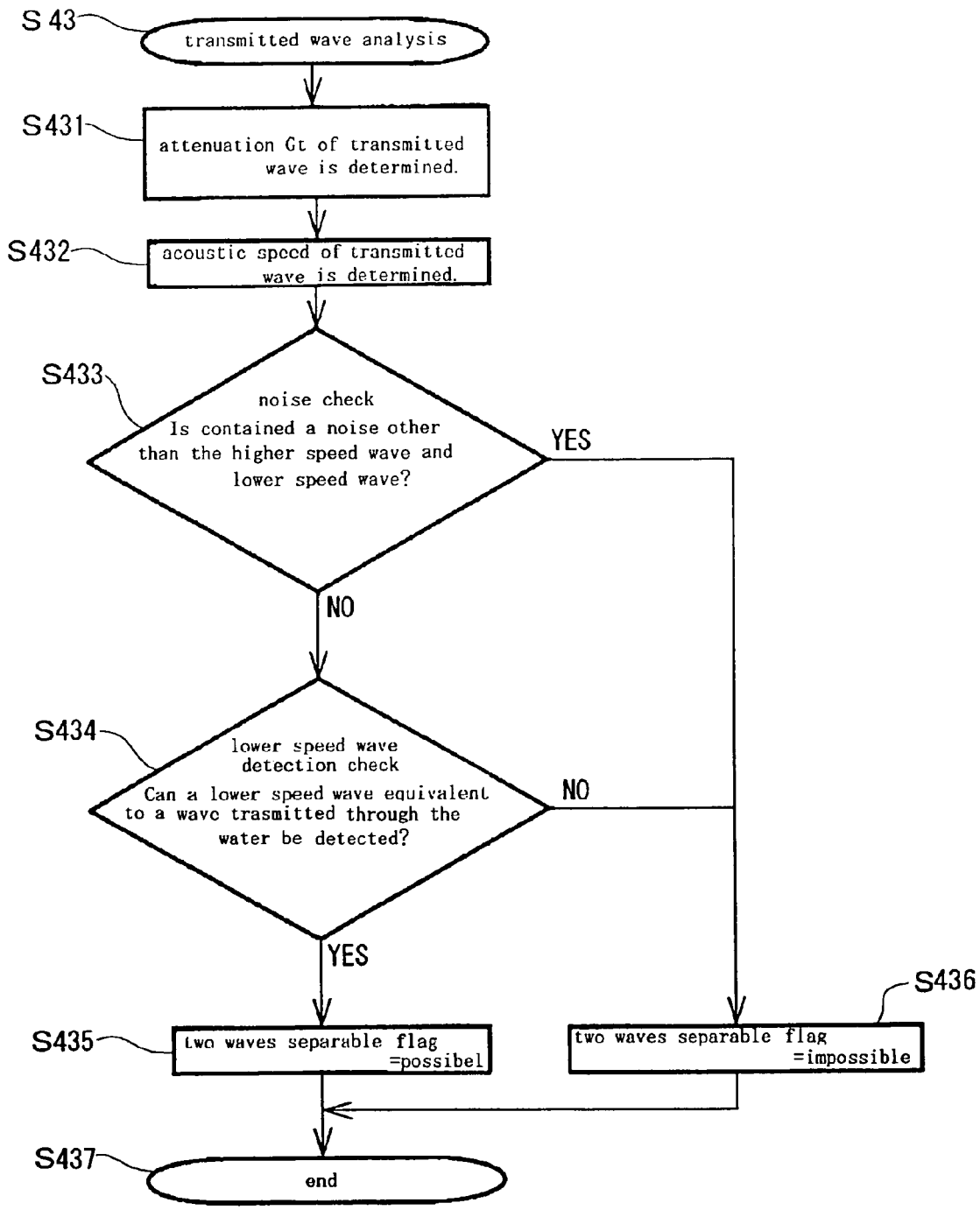
FIG. 8 is a flowchart for describing contents of a transmitted wave analysis in the first scanning.
Figure 9:
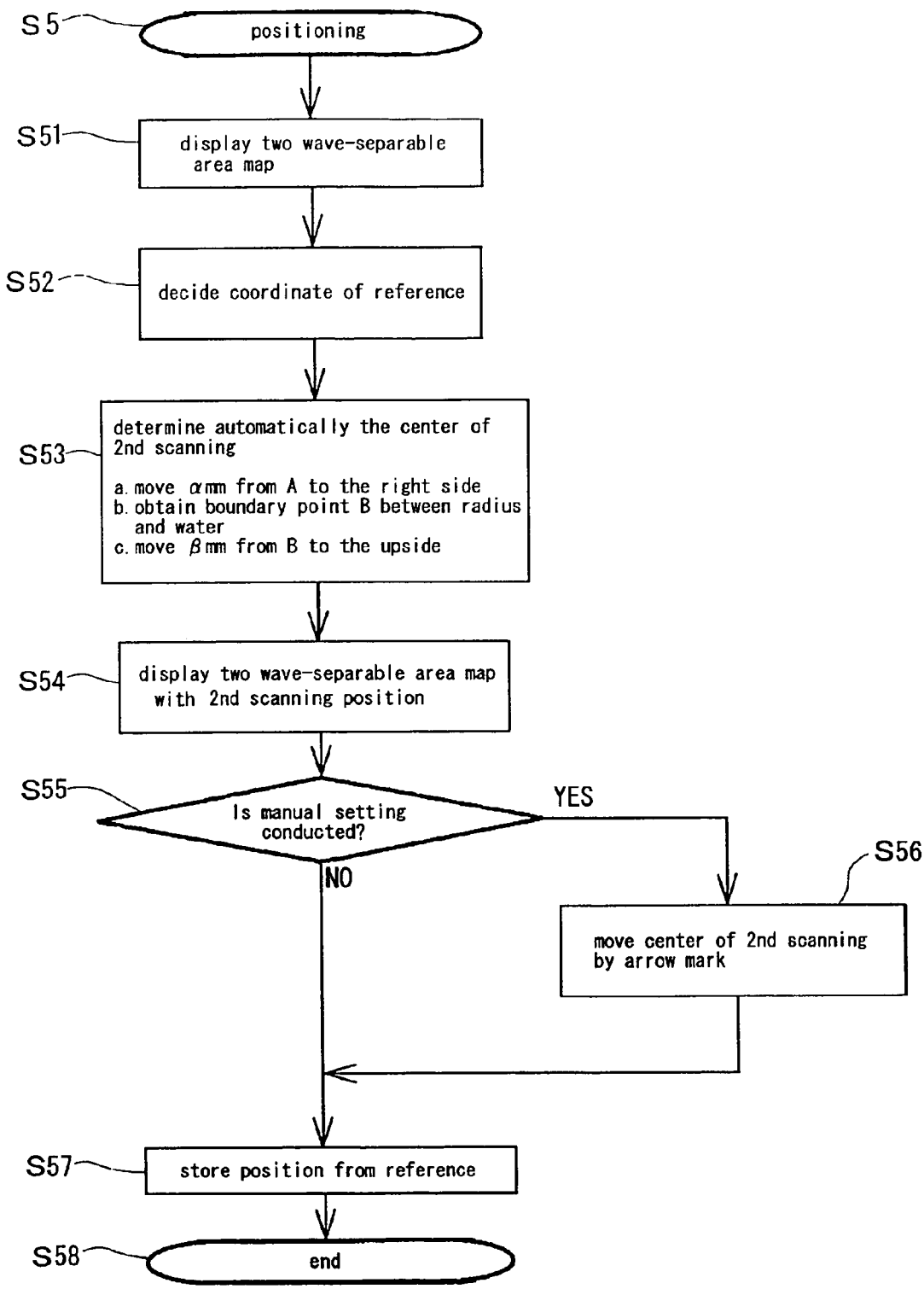
FIG. 9 is a flowchart for describing contents of positioning in the measuring procedure.
Figure 10:
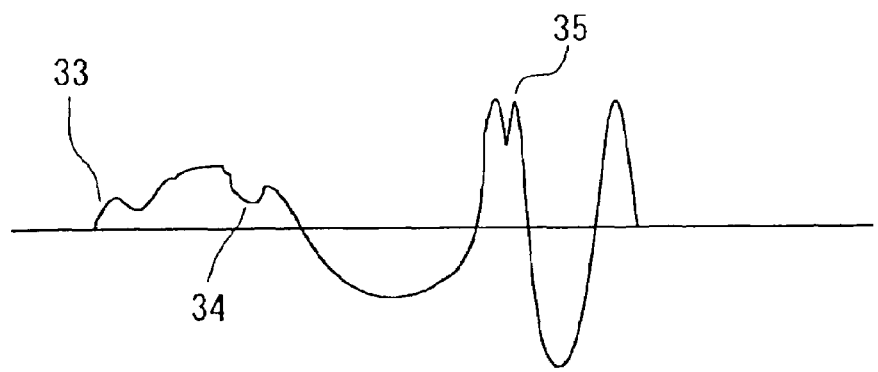
FIG. 10 is a graph for describing an example of a noise checking method.

Detailed description will be given of an example of a procedure for conducting measurement of a bone strength of a wrist 1 using the bone strength measuring instrument 10 with reference to FIGS. 5 to 13. FIG. 6 is a flowchart for describing an example of an overall procedure for conducting measurement of a bone strength using a bone strength measuring instrument 10 of the invention and FIGS. 7 to 9 are flowcharts for describing specific steps of the procedure in a further detailed manner.

As shown in FIG. 6, inputted into the operation display 12 prior to measurement are information on a patient, for example examination information on an individual including a name, a sex and an age and the like (step S1).

Then, the ultrasonic probes 5 and 6 are brought into close contact with each other by a manual operation, that is in a state where no wrist 1, which is a measurement site, exists, in which state an ultrasonic wave is transmitted and received between the ultrasonic probes 5,6, and signals received by the ultrasonic probes 5 and 6 are sent to the operation display 12 for processing to thereby perform calibration by picking up a predetermined background value (step S2) and to obtain an amplitude Lw in the matching water of the transmitted wave. Then, it is determined whether or not a prescribed calibration has been performed (step S3) and if the prescribed calibration has been performed, the process goes to preliminary measurement (a first scanning as step S4).

The preliminary measurement is conducted in order to determine a measurement region M in conducting the main measurement (a second scanning) with good precision, and since in the example, a measurement site is a wrist 1, a connection point A between the radius 24 and ulna 25 is obtained as the start point to determine the measurement region M (see FIG. 12) in the main measurement. Detailed description will be given of an example of the first scanning with reference to FIG. 7.

The preliminary measurement is conducted, for example, as described below. First of all, the ultrasonic probes 5 and 6 are moved away from each other in opposite directions by a manual operation and the left wrist 1 of a patient 8 is inserted therebetween. Since a prescribed matching water is supplied all the times to the ultrasonic probes 5 and 6 from the matching water supply section 14, the bodies of the probes make a slight, elastic deformation so as to be adapted for a thickness of a site of the wrist 1 held between the probes to thereby produce a state where the ultrasonic probes 5 and 6 are brought into close contact with both surfaces of the wrist 1.

In the state where the ultrasonic probes 5 and 6 are brought into close contact with both surfaces of the wrist 1, the measurement site is scanned with the ultrasonic probes 5 and 6 maintaining a state of facing each other at proper spacings in directions, above to below and left to right. To be more concrete, as shown in FIG. 5, scanning is performed on a measurement site (in the figure, a portion constructed with adjoining square cells) IA having longitudinal and lateral sides of 28 mm each at 15×15 points on the site with spacings each of 2 mm longitudinally and laterally, that is so as to cover 225 points on the site (step S41) and during the scanning, the ultrasonic waves are transmitted or receives by the ultrasonic probes 5 and 6 (step S42). Note that the measurement site 1A shown with a collection of square cells in FIG. 5 is actually shown with 10×10 points for convenience's sake.

In transmission or reception of an ultrasonic wave, an ultrasonic wave emitted from one ultrasonic wave probe 5 (or 6) is transmitted through tissues of a human body such as the cancellous bone 2, the cortical bone 3 and the soft tissue 4 in a wrist 1 and received by the other ultrasonic probe 6 (or 5) (step S42). The transmitted wave is attenuated in hard tissue portions such as the cancellous bone 2 and cortical bone 3, while being almost not absorbed in the soft tissue 4 and the matching water and being almost not attenuated. Therefore, signals received by the ultrasonic probes 5 and 6 are sent to the operation display 12 to receive a transmitted wave analysis (step S43). The transmitted wave analysis is conducted by attenuation of a transmitted wave for confirming a two-dimensional distribution of tissues of a wrist 1 in vivo. Description will be given of the transmitted wave analysis with reference to FIGS. 8, 10 and 11.

In the transmitted wave analysis (step S43), an attenuation Gt of a transmitted wave is determined as shown in FIG. 8 (step S431). That is, if an amplitude of a transmitted wave transmitted through a wrist 1 is indicated with L by definition and by performing an operation on the amplitude L and an amplitude Lw in the matching water of a transmitted wave obtained in a calibration (step S2) using the following equation (5), an attenuation Gt is obtained at each of points obtained in the first scanning.

$$Gt=20\times\log 10(L/Lw) \quad (5)$$

An acoustic speed of a transmitted wave is determined from a distance between the ultrasonic probes 5 and 6 and a propagation time of the transmitted wave (step S432).

In a case where, as described above, an ultrasonic wave is transmitted through the cancellous bone, an acoustic speed is different between when the wave is transmitted through a porous structure portion and when the wave is transmitted through a bone marrow structure portion; therefore, an ultrasonic wave emitted from one ultrasonic probe 5 (or 6) is separated into two different acoustic waves, that is a fast wave and a slow wave. Therefore, a noise check is performed on whether or not a noise other than the fast wave and slow wave is contained (step S433), and if it is determined that no noise exists, the process goes to the next step S434 and a slow wave detection check is performed on whether or not a waveform of the slow wave equivalent to a waveform of a wave transmitted through the matching water and if it is determined that the slow wave equivalent to a wave transmitted through the matching water can be detected, it is determined that the two waves including the fast wave and slow wave can be separated from each other (step S435).

On the other hand, if it is determined that a noise other than the fast wave and slow wave is contained in the noise check in step S433, or if the slow wave is not detected in the slow wave detection check in step S434 though it is not determined that a noise other than the fast wave and slow wave is contained, it is determined that the two waves including the fast wave and slow wave cannot be separated from each other (step S436).

As described above, in the transmitted wave analysis (step S43), it is determined whether or not a noise other than the fast wave and slow wave is contained in each signal obtained in the first scanning or it is determined whether or not the fast wave and slow wave can be separated from each other and the process goes to the next step S44 (step S437).

Figure 17A:
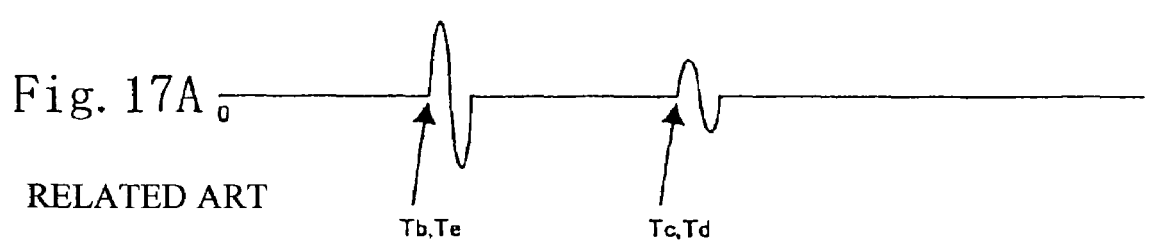
Figure 17B:
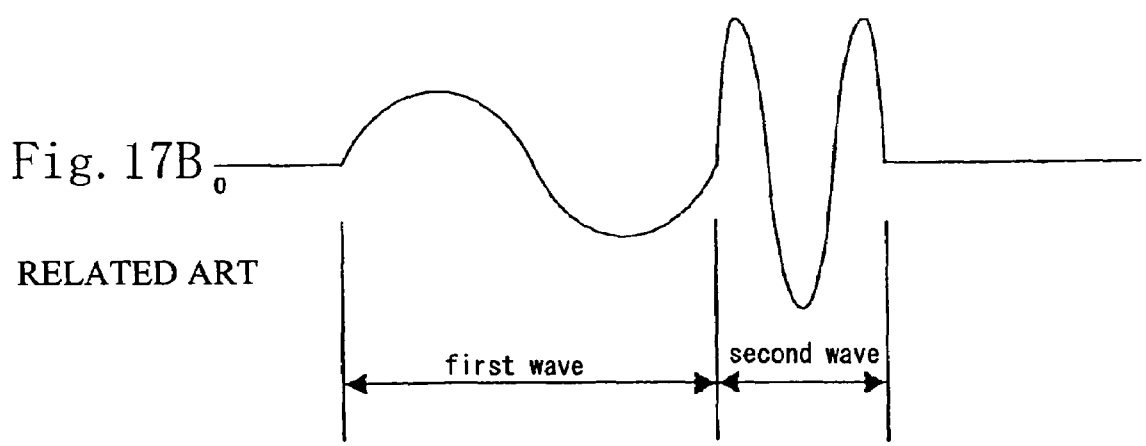

Then, description will be given of the noise check and the slow wave detection check. A waveform as shown, as a model, in FIG. 17(B) is a signal component passing through the shortest path (indicated with a symbol 7 in FIG. 16) between the ultrasonic probes 5 and 6 and a waveform passing through a path other than the shortest path because of reflection or refraction has in some case, for example, a peak and a dip as indicated with symbols 33, 34 and 35 in FIG. 10, which are determined as noises.

Figure 11A:
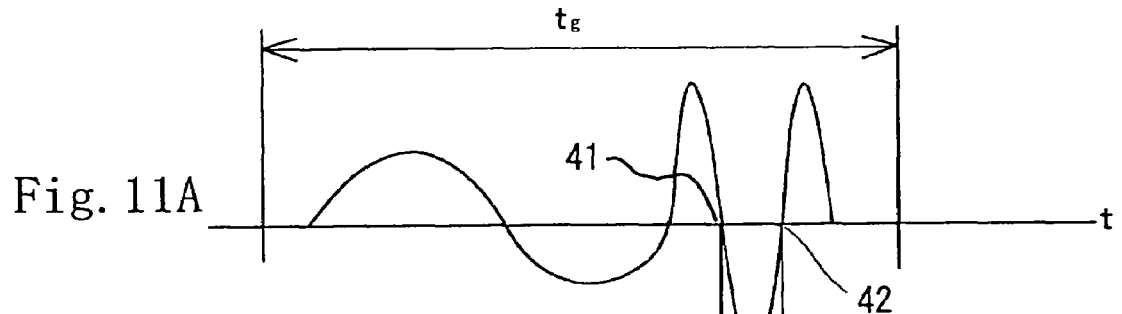
FIGS. 11(A) and 11(B) are graphs for describing an example of detection checking for a slow wave.
Figure 11B:
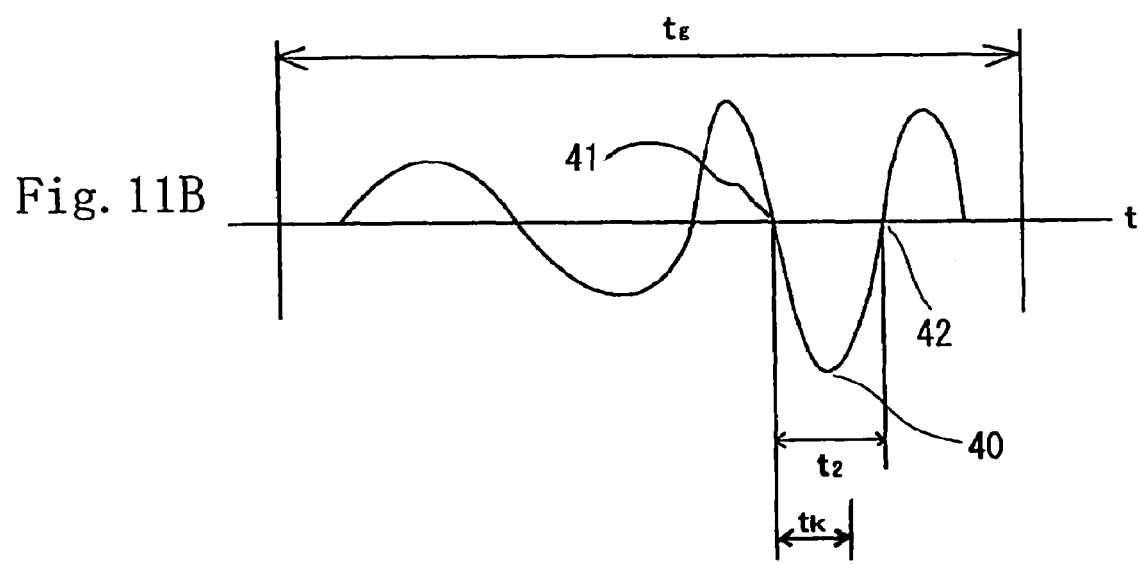

Then, the slow wave detection check is to check whether or not a slow wave with a waveform equivalent to that transmitted through a portion other than a bone such as the soft tissue 4 and water, which is performed as follows, for example:

1. Now, when a waveform as shown in FIGS. 11(A) and 11(B) exist, the maximum in absolute value of a negative value (in this example, a point indicated with a symbol 40) is detected in a gate tg with a proper width, which is determined part of the slow wave.

2. Zero cross points 41 and 42 on both sides of the point 40 showing the maximum in absolute value of a negative value are detected.

3. If a distance (a time width) t2 between the two zero cross points 41 and 42 is longer than a reference value tk (see FIGS. 11(A) and 11(B)), it is determined that no slow wave can be detected. For example, in the waveform shown in FIG. 11(A), since t2≦tk, it is determined that the slow wave can be detected, while in the waveform shown in FIG. 11(B), since t2>tk, it is determined that the slow wave cannot be detected.

Note that while description is given of the above checks using a waveform diagram for convenience's sake, checks similar to those are performed in a state of digital signals after AD conversion in a bone strength measuring instrument of the invention.

Figure 12:
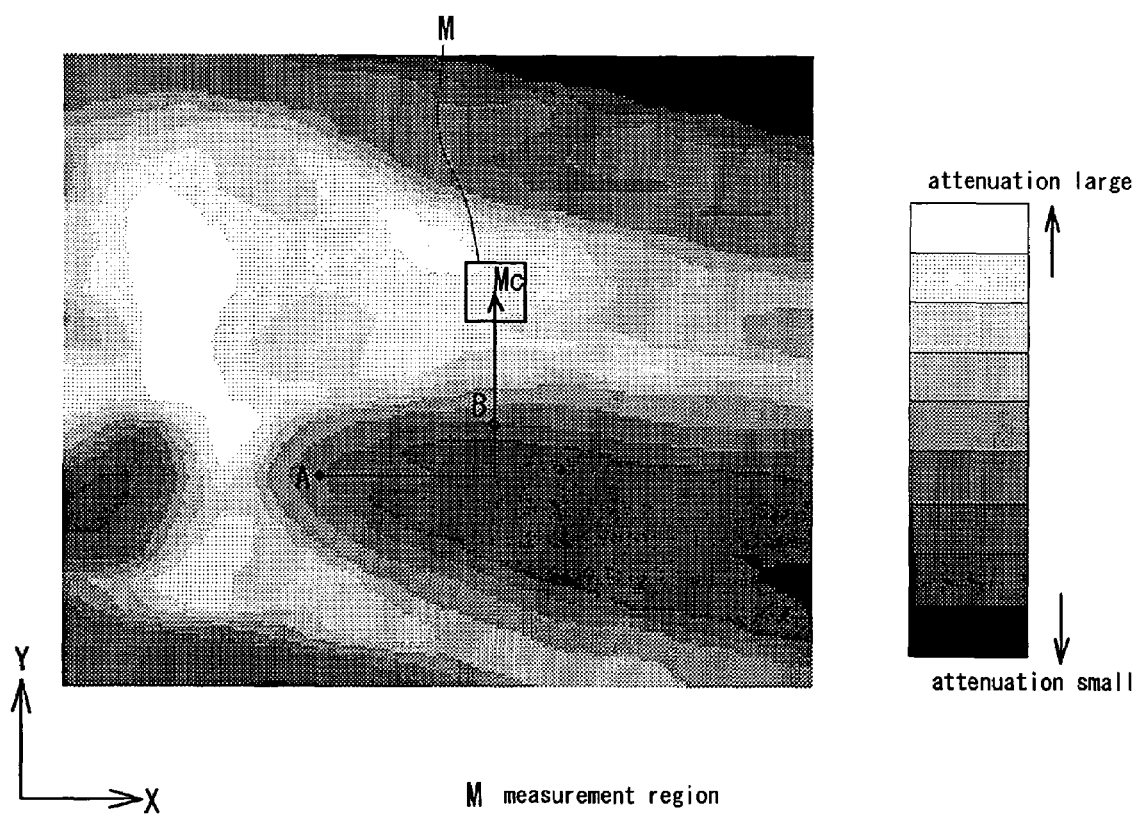
FIG. 12 is a representation showing an example of an attenuation map.

Again in FIG. 7, an analysis is performed on a transmitted wave at each of the 225 (=15×15) as done above (step S43) and as a result, there can be obtained an attenuation map as shown in, for example, FIG. 12 (step S44). This is because, as described above, when a wrist 1 is irradiated with an ultrasonic wave, the ultrasonic wave is greatly attenuated in a bone portion, while being not so much attenuated in portions of the soft tissue and water. In this figure, a fairly white portion has a large attenuation, while a fairly black portion has a small attenuation. In other words, the fairly white portion is of a bone tissue and the fairly black portion is of a soft tissue or water portion. That is, the attenuation map teaches an outline of a distribution status including a bone portion and portions other than the bone portion in a wrist 1.

FIG. 13 is a two wave-separable area map, which shows a model of results obtained in the separability determining step between the fast wave and slow wave in the transmitted wave analysis at the 225 points. In the map, a symbol ○ indicates two wave separable, a symbol × two wave non-separable and a symbol – not measured.

The prescribed number of points (in the example, 225 points) are scanned and it is determined whether or not prescribed data has been obtained (step S45) and if the prescribed number of point data has been obtained, the first scanning ends (step S46).

The first scanning, which is a preliminary measurement as described above, is performed, as shown in the flowchart of FIG. 6, in order to obtain a measurement area M for a main measurement (the second scanning). The measurement area M is set to a considerably smaller range than the scanning area for the first scanning, wherein the 15×15 points with 2 mm spacing are adopted in the first scanning, while 5×5 points with 1 mm spacing are adopted in the second scanning. In order to determine a measurement site (a so-called positioning) that seems to be the most preferable as the measurement region M for the second scanning, determination for the positioning (step S5) is performed based on the attenuation map shown in FIG. 12. Description will be given of an example of a procedure for the positioning with reference to the flowchart shown in FIG. 9.

In the positioning, as shown in FIG. 9, the two wave-separable area map is displayed (step S51).

Then, the connection point between the radius 24 and ulna 25 (hereinafter referred to as a reference) is obtained (step S52). The reference in the example is a point indicated with a symbol A shown in FIG. 12.

The center Mc of the measurement region M (measurement center) for the second scanning is automatically determined based on the reference A. As positioning methods for the measurement center, the following two methods are exemplified:

1. A method based on structural conditions.
2. A method based on the two wave separability determination.

The method based on structural conditions is conducted in a way described below. That is, a. the reference A is obtained from the attenuation map.

b. an X coordinate is determined at a point of a prescribed distance (for example, α mm) from the reference A to the right side.

c. the boundary point B between the soft tissue 4 and the radius 24 is obtained on a line upwardly passing through the X coordinate perpendicular thereto.

d. the measurement center Mc is determined at a point of a prescribed distance (for example, β mm) from the boundary point B on a line upwardly passing therethrough in the Y axis direction.

Then, the method based on the two wave separability determination is conducted this way: a proper point on the two wave separable area map is selected, it is determined whether or not separation into two waves can be effected at the selected point, if separation into two waves can be effected, the point is set to the measurement center Mc as it is, while if separation into two waves cannot be effected, it is determined whether or not separation into two waves can be effected at a point by, for example, 1 mm apart from the first point and selection of a new point at which separation into two waves can be effected is repeated till a point at which separation into two waves can be effected.

Note that in the example shown in FIG. 9, determination of the center point of the second scanning (step S53) is conducted according to the method (1) based on structural conditions.

After the second scanning position is determined, a two wave-separable area map with the second scanning position is displayed (step S54) and it is determined whether or not manual setting is conducted while the map is displayed (step S55). If the manual setting is selected (step S56), a result of the second scanning analysis can be obtained at a high probability since the center position of the second scanning can be set at a point where the two waves can be separated from each other.

After it is determined whether or not manual setting is conducted, positional data from the reference A is stored into a memory of the operation display 12(step S57) to complete the positioning (step S5). The positional data stored in the memory can be used in measurement on the same patient the next time.

After the positioning for the second scanning is completed according to the procedure as described above, the second scanning is, as shown in FIG. 6, conducted based on the positioning therefore (step S6). Since the second scanning is, as described above, conducted setting the measurement region M based on the first scanning, a desired measurement region M can be certainly irradiated with an ultrasonic wave.

After the prescribed second scanning ends, a result is displayed (step S7). It can be determined based on the result whether or not the second scanning should be repeated (step S8) and the second scanning can be repeated in a different measurement region M when required.

According to the fourth example, as described above, the main measurement based on the preliminary measurement can be conducted with certainty even in a simple manner and a bone strength measurement can be performed excellently in reliability and reproducibility.

In the fourth example, not only is the attenuation map indicating a degree of attenuation of a transmitted ultrasonic wave obtained by processing a signal obtained by the preliminary measurement, but it is also determined whether or not the first wave higher in speed and the second wave lower in speed, both being the ultrasonic transmitted waves, can be discriminated from each other and then, the measurement region M for the main measurement is set based on the determination and the attenuation map, while in setting of the measurement region M, it is also recommended to use the speed map indicating a distribution of speeds of the transmitted ultrasonic wave transmitted through part of a human body instead of the attenuation map as exemplified in FIG. 12.

Figure 14:
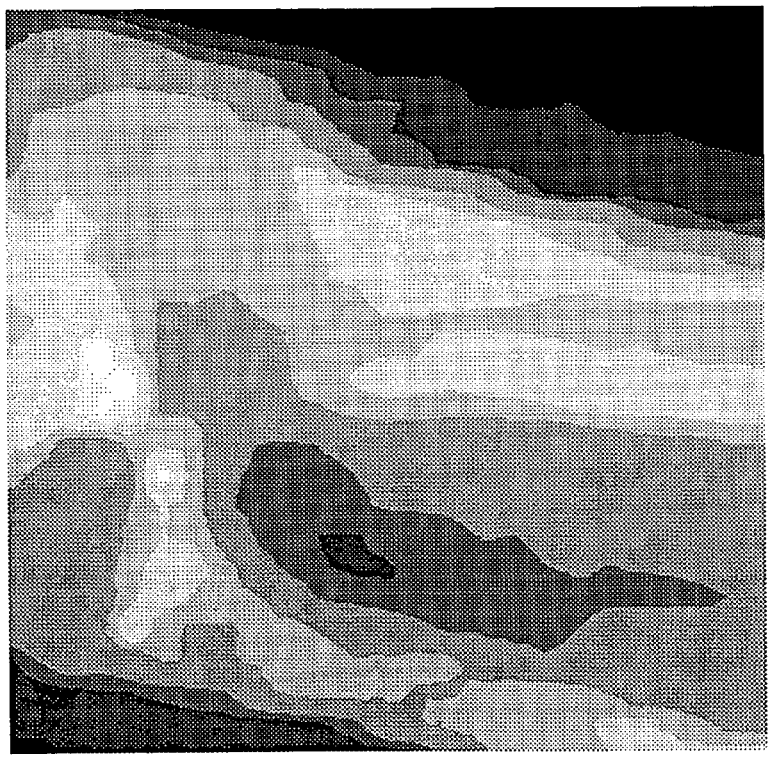
FIG. 14 is a representation showing an example of a speed map.
Figure 14:
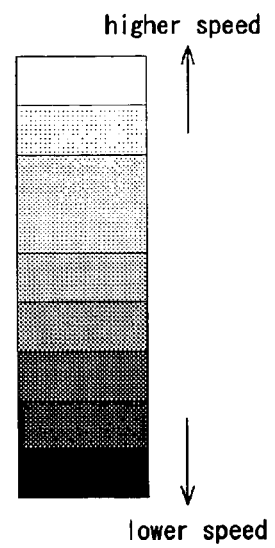
Figure 15:
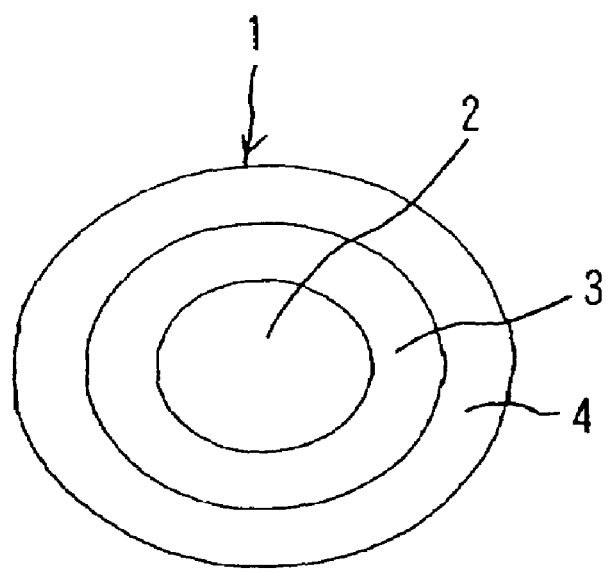
FIG. 15 is a model view showing a cross-sectional structure of a wrist.

That is, in the invention, as described above, the transmitted wave analysis is performed using signals obtained while the first scanning is conducted (see FIG. 7) and in the transmitted wave analysis, an acoustic speed of the transmitted wave is also determined as shown in FIG. 8. Determination of an acoustic speed of the transmitted wave can be achieved from a distance between the ultrasonic probes 5 and 6 and a propagation time of the transmitted wave, and for example, acoustic speeds can be obtained from data of all the respective 225 points; therefore, for example, the map, as shown in FIG. 14, indicating a distribution status of speeds of the transmitted wave can be obtained from data obtained by the first scanning. In the figure, a portion of a fairly white in color is a portion having a higher propagation speed of the transmitted wave, while a portion of a fairly black in color is a portion having a lower propagation speed of the transmitted wave. In other words, the portion of a fairly white in color is of a bone tissue and the portion of a fairly black in color is of the soft tissue or water. That is, there can be understood an outline of a distribution status of a bone portion and other portions in a wrist 1 from the speed map.

Therefore, the measurement region M can be set based on the speed map and determination on whether the first wave higher in speed and the second wave lower in speed, both being the transmitted ultrasonic waves, can be discriminated from each other. Since the action and effect in such a case are the same as in the case of the fourth example of which detailed description is given, detailed description thereof is omitted.

While in the examples, the ultrasonic probes 5 and 6 are used in two-dimensional scanning, the present invention is not limited thereto and the invention can be applied even to a so-called ultrasonic phased array type in a similar manner.

Those skilled in the art will appreciate that various adaptations and modifications of the just-described preferred embodiment can be configured without departing from the scope and spirit of the invention. Therefore, it is to be understood that, within the scope of the amended claims, the invention may be practiced other than as specifically described herein.

What is claimed is:

1. In a bone strength measuring instrument, which transmits/receives an ultrasonic wave to/from part of a human body in a state where the part of the human body is held between a pair of ultrasonic probes each containing an ultrasonic transmission/reception transducer and an acoustic impedance matching liquid, and processes signals generated upon transmission/reception of the ultrasonic wave, thereby measuring a bone strength in the part of the human body, the improvement comprising:

a calculating unit for determining, a first wave obtained from the ultrasonic wave probe and is high in speed upon passing through a cancellous bone and a second wave obtained from the ultrasonic wave probe and is low in speed thereupon, where in an acoustic speed Vs of the second wave in the cancellous bone has a constant value, an operation is performed using the constant value of acoustic speed Vs and arrival times Ts of the second wave to the ultrasonic wave probe, respective thickness values of a soft tissue, a cortical bone and the cancellous bone in the part of a human body.

2. In a bone strength measuring instrument, which transmits/receives an ultrasonic wave to/from part of a human body in a state where the part of the human body is held between a pair of ultrasonic probes each containing an ultrasonic transmission/reception transducer and an acoustic impedance matching liquid, and processes signals generated upon transmission/reception of the ultrasonic wave, thereby measuring a bone strength in the part of the human body, the improvement comprising:

a measuring unit for determining a first wave obtained from the ultrasonic wave probe and is high in speed upon passing through a cancellous bone and a second wave obtained from the ultrasonic wave probe and is low in speed thereupon, wherein an acoustic speed of the second wave has a constant value, arrival times Tc, Td of reflected waves reflected on a boundary between a cortical bone and the cancellous bone are measured, and determining by using the acoustic speed of the second wave and the arrival times of transmitted waves to obtain an acoustic speed in the cortical bone, a bone property of the cortical bone based on the acoustic speed Vbc, Vde in the cortical bone.

3. In a bone strength measuring instrument, which transmits/receives an ultrasonic wave to/from part of a human body in a state where the part of the human body is held between a pair of ultrasonic probes each containing an ultrasonic transmission/reception transducer and an acoustic impedance matching liquid, and processes signals generated upon transmission/reception of the ultrasonic wave, thereby measuring a bone strength in the part of the human body, the improvement comprising:

a measuring unit for determining a first wave obtained from the ultrasonic wave probe and is high in speed upon passing through a path in a cancellous bone and a second wave obtained from the ultrasonic wave probe and is low in speed thereupon, arrival times of the second wave and arrival times of reflected waves reflected on the boundary between a cortical bone and the cancellous bone, wherein a speed of the second wave in the cancellous bone is obtained using the arrival times, and determining a property and condition of the cancellous bone based on the acoustic speed of the second wave in the cancellous bone.

4. In a bone strength measuring instrument, which conducts a preliminary measurement prior to a main measurement transmitting and receiving an ultrasonic wave through part of a human body including the cancellous bone, sets a measurement region based on a result of this preliminary measurement, conducts the main measurement in the measurement region, processes a signal obtained in the main measurement in a logic and arithmetic operation section, and obtains information such as a bone strength in the part of a human body, the improvement comprising:

a measuring unit for processing a signal obtained in the preliminary measurement to thereby obtain an attenuation map indicating a degree of attenuation of a transmitted ultrasonic wave, and a determining whether or not the first wave higher in speed and the second wave lower in speed separated from the ultrasonic wave can be discriminated from each other, wherein the measurement region for the main measurement is set based on the determination and the attenuation map.

5. In a bone strength measuring instrument according to claim 4, wherein a distance of a center of measurement region from a connection point between a radius and ulna obtained based on the attenuation map in setting of the measurement region for the main measurement is stored and the distance is used in setting of a measurement region for the next measurement, in a case where the part of a human body is a wrist.

6. In a bone strength measuring instrument, which conducts a preliminary measurement prior to a main measurement transmitting and receiving an ultrasonic wave through part of a human body including the cancellous bone, sets a measurement region based on a result of this preliminary measurement, conducts the main measurement in the measurement region, processes a signal obtained in the main measurement in a logic and arithmetic operation section, and obtains information such as a bone strength in the part of a human body, the improvement comprising:

a measuring unit for processing a signal obtained in the preliminary measurement to thereby obtain a speed map indicating a speed distribution of a transmitted ultrasonic wave passing through the part of a human body, and also determined whether or not a first wave higher in speed and a second wave lower in speed from the ultrasonic wave can be discriminated from each other, wherein the measurement region for the main measurement is set based on the determination and the speed map.

7. In the bone strength measuring instrument according to claim 6, wherein a distance of a center of measurement region from a connection point between a radius and ulna obtained based on the speed map in setting of the measurement region for the main measurement is stored and the distance is used in setting of a measurement region for the next measurement, in a case where the part of a human body is a wrist.

8. In a method of measuring bone strength by transmitting and receiving an ultrasonic wave to and from a portion of a human body and providing signals representative of such measurement, the improvement comprising:

applying ultrasonic waves to the portion of human body;

obtaining the thickness of the human body and the soft tissue by using arrival times of reflected waves;

obtaining from the transmitted ultrasonic wave a first wave signal of high speed in passing through cancellous bone and a second wave signal of low speed;

setting the measured acoustic speed of the second wave signal in the cancellous bone as a constant value; and processing the human body portion thickness and the soft tissue thickness, the measured arrival times of the second wave signal and the acoustic speeds of the second wave signal to determine the respective thickness values of cortical bone and cancellous bone in the portion of the human body.

9. In a bone strength measuring instrument which transmits and receives an ultrasonic wave to and from a portion of a human body and provides signals representative of such measurement, the improvement comprising:

means for applying ultrasonic waves to the portion of human body;

means for obtaining the thickness of the human body and the soft tissue by using arrival times of reflected waves;

means for obtaining from the transmitted ultrasonic wave a first wave signal of high speed in passing through cancellous bone and a second wave signal of low speed;

means for setting the measured acoustic speed of the second wave signal in the cancellous bone as a constant value; and means for processing the human body portion thickness and the soft tissue thickness, the measured arrival times of the second wave signal and the acoustic speeds of the second wave signal to determine the respective thickness values of cortical bone and cancellous bone in the portion of the human body.

* * * * *